United States Patent [19]

Warriner

[11] Plant 5,250

[45] Jun. 26, 1984

[54] ROSE PLANT—JACROM

[75] Inventor: William A. Warriner, Tustin, Calif.

[73] Assignee: Jackson & Perkins Company, Medford, Oreg.

[21] Appl. No.: 428,316

[22] Filed: Sep. 29, 1982

[51] Int. Cl.[3] ..... A01H 5/00

[52] U.S. Cl. ..... Plt./18

[58] Field of Search ..... Plt./17–18

*Primary Examiner*—Robert E. Bagwill

*Attorney, Agent, or Firm*—Klarquist, Sparkman, Campbell, Leigh & Whinston

[57] ABSTRACT

A hybrid tea rose variety having orange-red bud and bloom color, pointed bud form, straight and stiff stems, and large foliage.

1 Drawing Figure

1

This present invention relates to a new and distinct variety of rose plant of the hybrid tea class which was originated by me by crossing an unnamed variety with the variety Prominent, U.S. Plant Pat. No. 3,380.

The primary objective of this breeding was to produce a new rose variety in the light orange color range with good characteristics for use as a cut flower. This objective was substantially achieved along with other desirable improvements as evidenced by the following unique combination of characteristics which are outstanding in the new variety and which distinguish it from its parents, as well as from all other varieties of which I am aware:

1. An orange-red bud and bloom, RHS 35 and 42.
2. A pointed bud form, desired in cut roses.
3. Non-blueing color in aging flowers.
4. Straight, stiff stems, mostly in 22"–26" lengths.
5. Large, attractive foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Prominent, U.S. Plant Pat. No. 3,380.

Classification:

*Botanical.*—Rosa hybrid.

*Commercial.*—Hybrid tea.

FLOWER

Observations made from specimens grown in a greenhouse at Irvine, Calif. in August, 1982.

Blooming habit: Continuous.

Bud:

*Size.*—1¼" when petals start to unfurl.

*Form.*—Long, pointed ovoid.

2

*Color.*—When sepals first divide, near 48B, Red Group. When half blown; upper side of petals near 42D, Red Group; lower side of petals near 42D, Red Group.

*Sepals.*—Color: Outer surface Green Group, 138A. Surface has few stipitate glands near base. Three appendaged sepals lightly appendaged. Two unappendaged sepals hairy edged.

*Receptacle.*—Color: Green 138A. Shape: Funnel. Size: Large. Surface: Nearly smooth.

*Peduncle.*—Length: Long. Surface: Prickly. Color: Light green. Strength: Stiff, erect.

*Opening.*—Petals curl back on edges.

Bloom:

*Size.*—Medium. Average open size is 3½".

*Borne.*—Singly.

*Stems.*—Long, strong.

*Form.*—When first open, high center. Permanence: Outer petals curl back.

*Petalage.*—Number of petals under normal conditions: 23–35.

*Color.*—Center of flower: Upper side of petals near Orange-Red 35C; reverse side of petals near Orange-Red 35D; base of petals near White. General tonality from a distance near Orange-Red 35D.

*Variegations.*—None.

*Discoloration.*—General tonality at end of first day: No change. Third day: Color fades slightly to Orange-Red 35D.

*Fragrance.*—None.

Petals:

*Shape.*—Nearly round.

*Form.*—Edges slightly quilled.

*Arrangement.*—Irregular. Petaloids in center, few.

*Persistence.*—Drop off cleanly.

*Lastingness.*—On the plant, long. As cut flower, long.

Reproductive parts:

*Anthers.*—Large. Color: Orange-Yellow 14C. Arrangement: Regular around styles.

*Filaments.*—Color: White.

*Pollen.*—Lemon yellow.

*Styles.*—Color: Near white.

*Stigmas.*—Color: Near white.

PLANT

Form: Bush.

Growth: Very vigorous, upright.

Foliage: Number of leaflets on normal mid-stem leaves: 5 or 7.

*Size.*—Large.

*Quantity.*—Normal.

*Color.*—New foliage: Greyed Purple 187A. Old foliage: Green 137A.

Leaflets:

*Shape.*—Oval pointed.

*Texture.*—Upper side: Leathery.

*Edge.*—Serrated.

*Serration.*—Single, small.

*Petiole.*—Rachis: Color: Green. Underside: Few prickles.

*Stipules.*—Medium.

*Disease resistance.*—Slightly susceptible to mildew, blackspot under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalk, ordinary.

*Form.*—Long, straight.

*Color when young.*—Brown.

*Position.*—Irregular.

Small prickles:

*Quantity.*—On main stalks, few. On laterals, few.

*Color.*—Brown.

I claim:

1. A new and distinct variety of rose plant of the hybrid tea class, substantially as herein shown and described, characterized particularly as to novelty by the unique combination of its pointed bud of a light orange color, non-blueing in age, on long straight stems, usable as cut flowers.

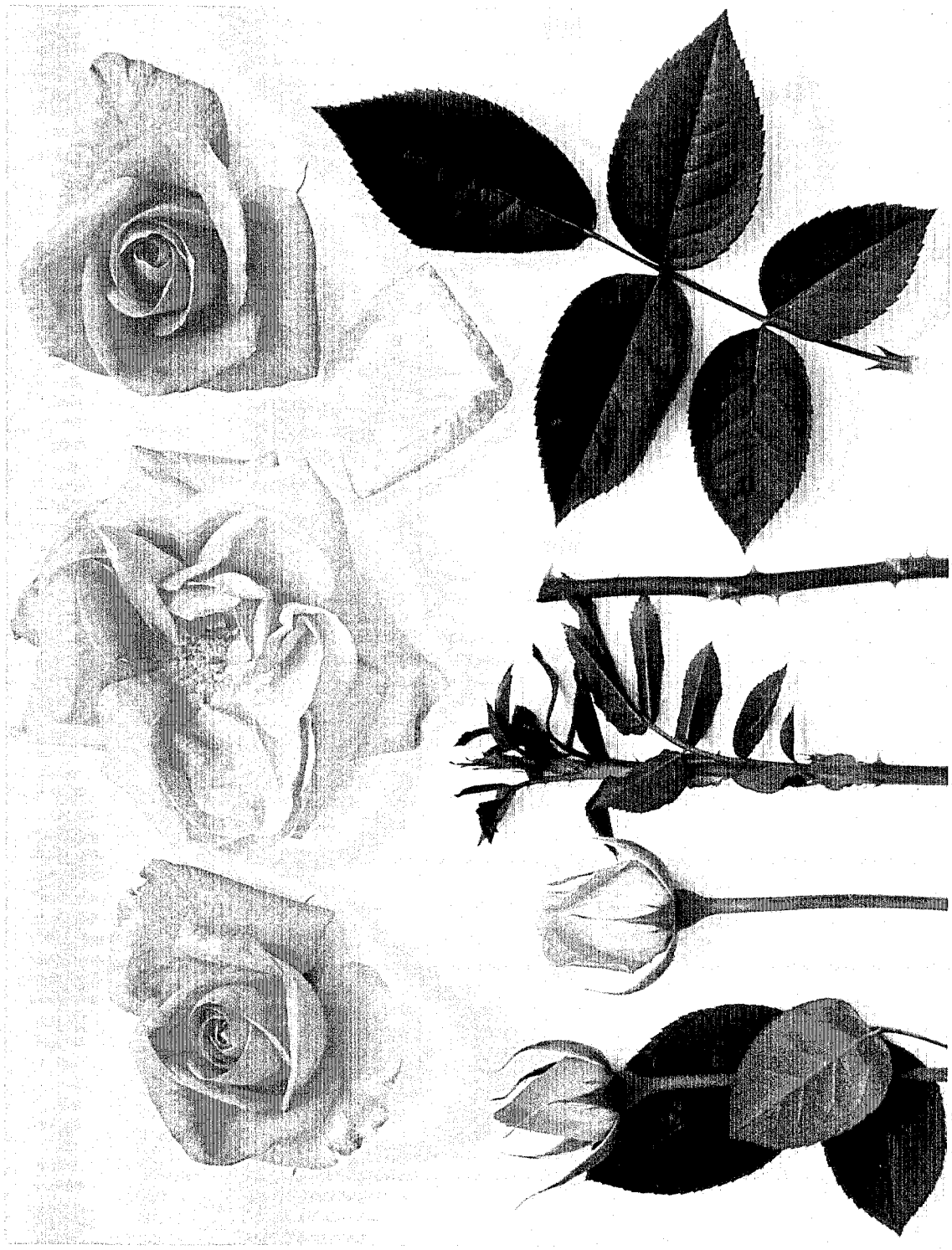

* * * * *